United States Patent [19]
Dyck

[11] 3,982,544
[45] Sept. 28, 1976

[54] DEVICE FOR EVERTING A PROBE INTO A BODY CAVITY

[75] Inventor: Manfred Dyck, Somerville, N.J.

[73] Assignee: Johnson & Johnson, New Brunswick, N.J.

[22] Filed: Nov. 18, 1974

[21] Appl. No.: 524,610

[52] U.S. Cl............................. 128/349 R; 128/262; 128/349 B
[51] Int. Cl.²........................................ A61M 25/00
[58] Field of Search............ 128/348, 349 R, 349 B, 128/349 BV, 350 R, 351, 2 R, 2 M, 262

[56] References Cited
UNITED STATES PATENTS

| | | |
|---|---|---|
| 3,010,453 | 11/1961 | Doherty............................ 128/214.4 |
| 3,050,066 | 8/1962 | Koehn.............................. 128/349 B |
| 3,168,092 | 2/1965 | Silverman....................... 128/262 X |
| 3,433,215 | 3/1969 | Silverman....................... 128/262 X |
| 3,502,069 | 3/1970 | Silverman....................... 128/262 X |
| 3,703,174 | 11/1972 | Smith.............................. 128/214.4 |
| 3,911,927 | 10/1975 | Rich et al........................ 128/349 R |

*Primary Examiner*—Dalton L. Truluck
*Attorney, Agent, or Firm*—Steven P. Berman

[57] ABSTRACT

A device for providing a double-walled annular pressurized probe into a body cavity is provided comprising a pressurizing chamber in flow communication with an adapter. The probe is sealed to one end of the adapter and means are provided for everting the probe from the adapter into a body cavity while also sealing the pressurized annulus.

8 Claims, 8 Drawing Figures

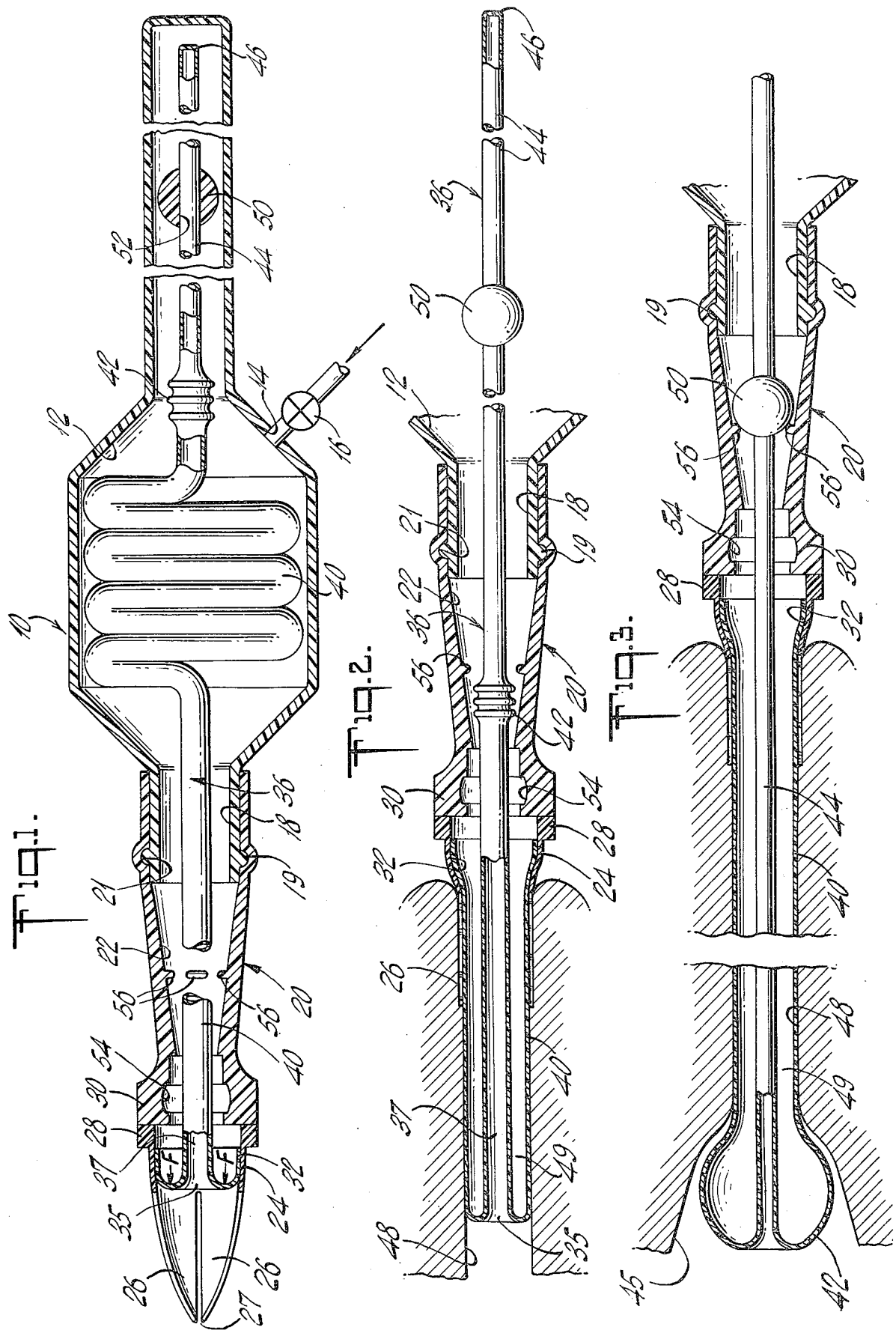

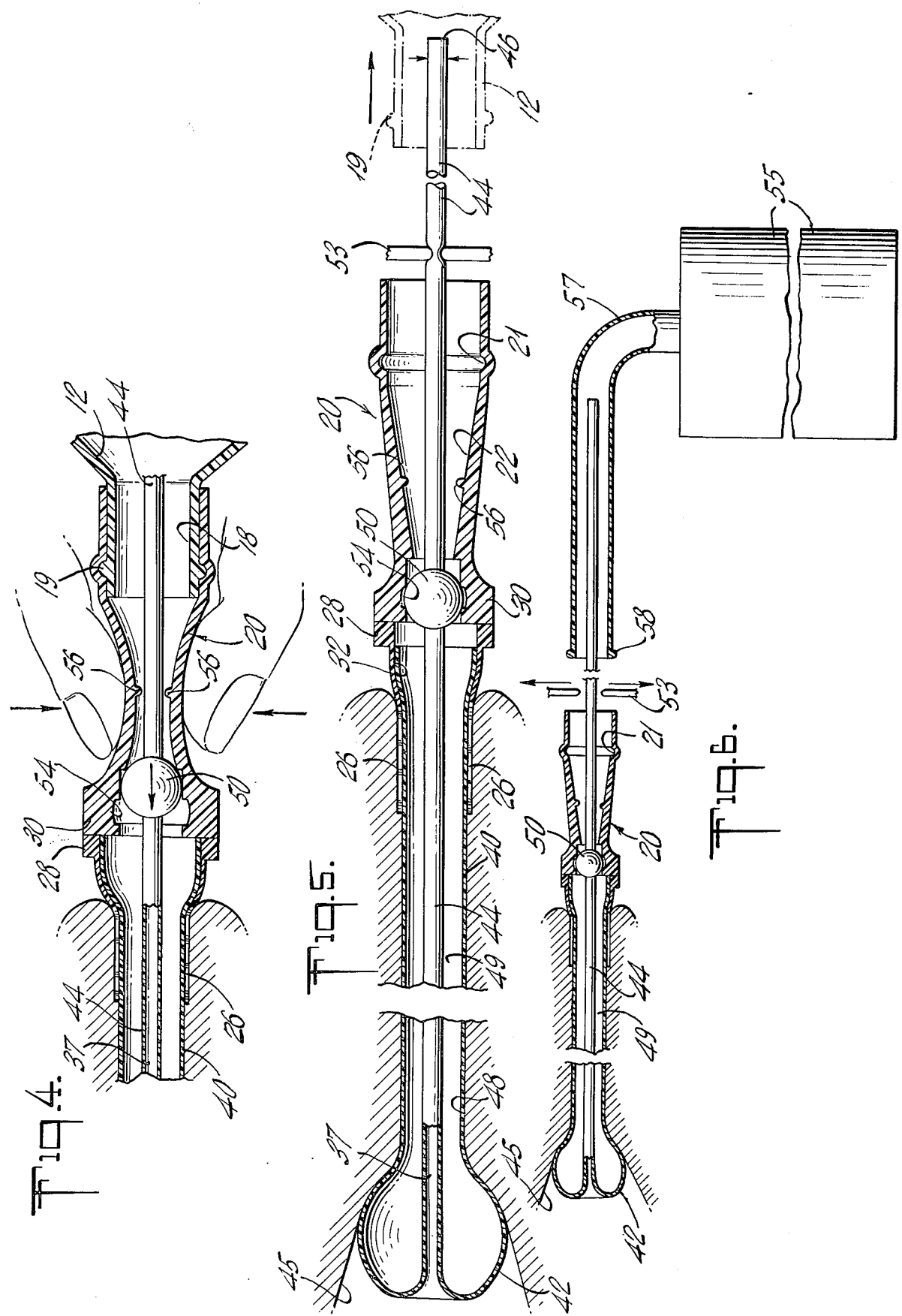

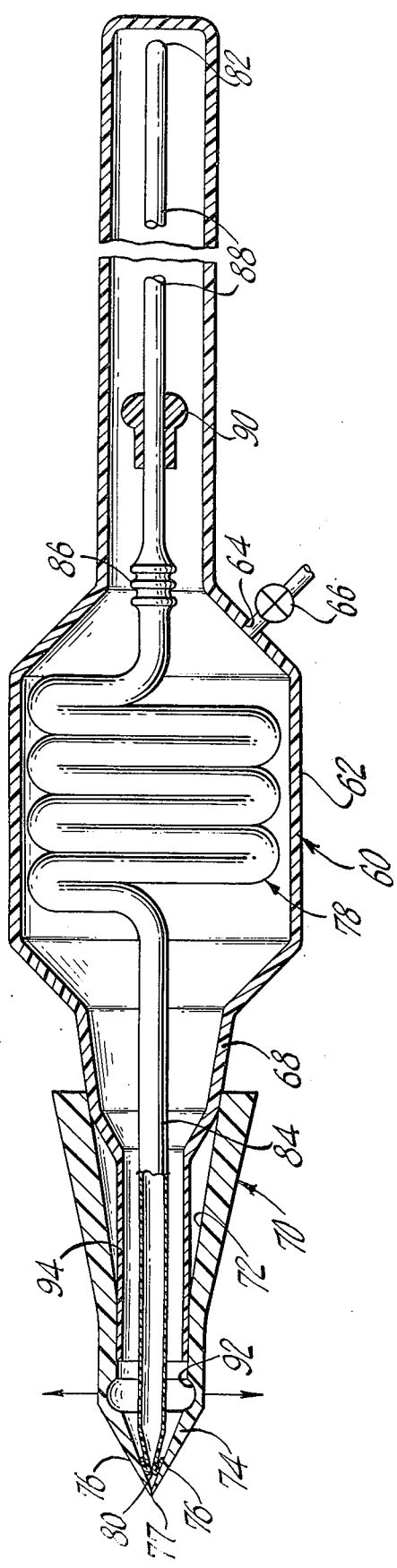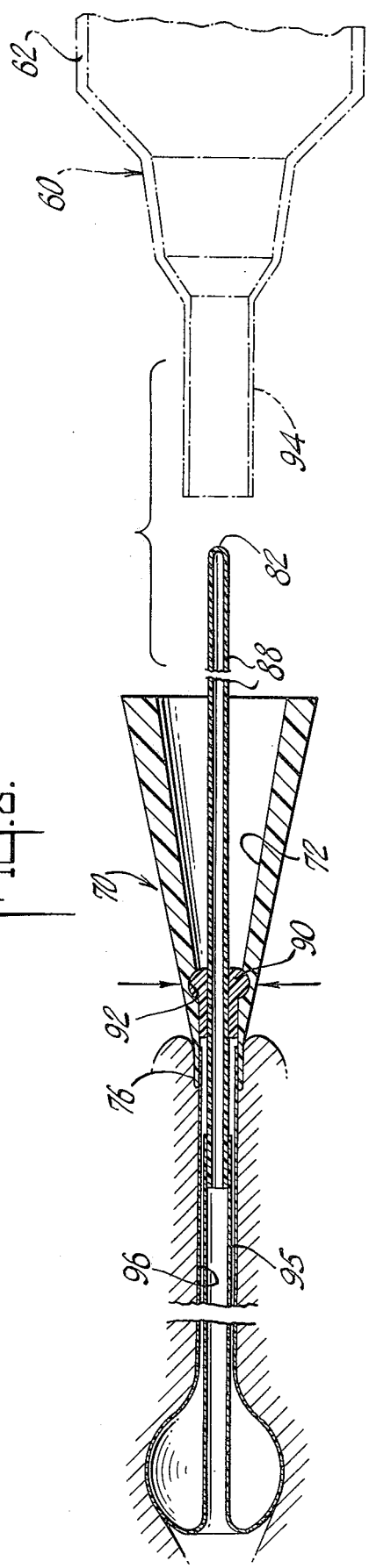

DEVICE FOR EVERTING A PROBE INTO A BODY CAVITY

BACKGROUND OF THE INVENTION

This invention relates to tubular probes and devices for delivering said probes into body cavities. Such probes most prevalently find use as catheters and specifically, urinary catheters which are used for a variety of medical reasons such as to drain the bladder of accumulated urine, to introduce medication, to lavage, to correct physiological defects and to ascertain urinary output.

The commonly used catheter consists of a simple single-walled tube or, in the case of a retention catheter, a single-walled tube along side a second tube through which a fluid is provided for inflating a retention balloon, this latter type known generally as a Foley catheter. These catheters are emplaced by sliding the same into a body passage in a process which is both difficult for the doctor and painful for the patient. Recently, it has been discovered that a new form of urinary catheter may be inserted by the method of "eversion", obviating the sliding method of insertion and greatly facilitating the emplacement process. As applied to this instant invention, the eversion method is utilized in a device wherein a tube is placed in a pressurizing chamber having an opening at one end. One end of the tube is sealed across this opening. In operation, the chamber is pressurized with a fluid such as water, the pressurizing fluid exerts a force across the opening of the chamber and pushes the tube out of the chamber and into the body cavity. Because one end of the tube is fixed across the opening of the chamber, the tube is forced out of the chamber in a double-walled configuration wherein the annulus is filled with pressurizing fluid and the center, void of such fluid, provides a conduit for the usual catheter purposes.

While this eversible probe greatly alleviates the discomfort and difficulties concomitant with medical procedures such as catheterization, the device is considerably more complex than the simple catheters used heretofore and such complexity generates drawbacks. One particularly difficult problem associated with the use and design of these eversible catheters is the difficulty in sealing the pressurized annulus after the probe has been completely everted. At that point in time, it is desirable to remove the pressurizing chamber from the tubing and at the same time, maintain a sealed annulus. Another problem is that, as with present urinary catheter systems, as soon as the probe penetrates the sphincter muscle and enters the trigone area of the bladder, there is an immediate flow of urine into the conduit. Thus, it is necessary to provide a sealing means to preclude uncontrolled flow of urine at this point in time. Because of the complex nature of the eversible catheter, no truly satisfactory method has heretofore been available for sealing the annulus and precluding the premature flow of urine.

SUMMARY OF THE INVENTION

This instant invention is therefore directed toward improvements in a device for delivering a double-walled probe into a body cavity by the method of eversion and specifically to provide simple means for sealing the annulus of the everted probe and precluding premature flow of urine when the device is used for urinary catheterization.

The device comprises a pressurizing chamber having an inlet port for introducing a pressurizing fluid therein. An adapter, preferably having a conical shape, is provided with an axial bore therethrough having first and second open ends and is removably attached to the pressurizing chamber so that the bore is in flow communication therewith. An eversible tube is provided having one end closed and the other end open; the open end being sealed to the adapter, across the adapter bore, the sealing thus precluding the unrestricted flow of pressurizing fluid from the chamber and out of the adapter, i.e., the flow of fluid out of the adapter (unrestricted by the annular walls of the double-walled probe after it is everted into a body cavity) is precluded by the tube sealed across the bore. The remainder of the tubing extends through the adapter bore from the sealing point and back into the chamber.

It will therefore be understood that, upon pressurizing the chamber with fluid, the tubing, being sealed across the adapter bore, thus restricts the free flow of fluid and causes the fluid instead to bear against the tubing, urging the tubing out of the bore of the adapter in the form of a double-walled probe, the annulus of which is filled with the pressurizing fluid.

Once the tube is fully everted, it is desirable to detach and discard the cumbersome chamber from the adapter. Before this can be accomplished, it is necessary to seal the pressurized annulus to avoid the collapse of the double-walled probe. In accordance with this invention, a value is provided, carried on the tube near the closed end thereof. Preferably, this valve is spherical in shape and has a bore therethrough. The tube is drawn through the bore and the valve may be readjusted to a desired position on the tube. This position is chosen so that when the tube is essentially completely everted, the valve has been carried along with the tube to a point within the bore of the adapter. Means are provided for seating the valve so as to seal the annulus; these means comprise having the adapter constructed from a flexible, elastically resilient material and having a valve seat provided in the inner walls of the adapter bore. The valve seat is sized so as to be, at its smallest cross section, smaller than the largest cross section of the valve when the elastically resilient adapter is in a relaxed condition. Thus, when the valve is seated in the seat and the pressurizing chamber is detached from the adapter, a tight annulus seal will be effected by the valve seat stretehed or flexed about the valve.

In a first specific embodiment, the elastically resilient adapter may be removably attached to the pressurizing chamber in a relaxed condition. The valve may then be seated in the valve seat by the application of pressure on the outside walls of the adapter bore as with a tool or more simply by squeezing the walls of the adapter together between two fingers and forcing the valve in the seat.

In a second embodiment, the valve may be seated by means which again comprise having the adapter constructed from a flexible, elastically resilient material and having a valve seat provided in the inner walls of the adapter bore. In this embodiment, however, the adapter is connected to the pressurizing chamber and flexing means are provided for maintaining the adapter in a flexed state so that the valve seat is flexed to a size larger than the valve. The flexing means may comprise having the pressurizing chamber terminate in a nozzle and stretching the flexible resilient material of the adapter to fit over the nozzle thereby enlarging the bore of the adapter throughout its length. Because of this enlargement, the valve, carried along with the tubing into the bore of the adapter, is free to be carried loosely into the valve seat. Upon thereafter detaching the adapter from the nozzle of the pressurizing chamber, the stretched adapter will relax, the enlarged bore will tend to contract back to its relaxed position and the valve seat will close upon the valve thereby sealing the annulus, all of the above occurring substantially simultaneously with the detachment of the adapter from the chamber.

In more specific embodiments of the invention, the valve seat comprises a circumferential groove in the inner wall of the bore of the adapter, the groove having a concave radius which is no greater than the radius of the valve whereby the valve makes two, circumferential-line contacts with the valve, providing a positive seal for the annulus.

In still more specific embodiments, means are provided on the inner walls of the axial bore to temporarily restrain the valve before it reaches the valve seat and therefore apprise the operator of the device that the valve is in a position for seating. This temporary restraint of the valve also allows the operator to provide additional pressurizing fluid to fully complete the eversion process if so desired. These means may comprise providing at least one and preferably, a plurality of thin, flexible projections or stops circumferentially arranged around the inner wall of the bore and projecting inwardly so as to restrict the further movement of the valve. The restriction, however, owing to the flexible nature of the stops and the material of construction of the adapter, can be easily overcome by exerting pressure, behind the valve, on the outer walls of the adapter, thus urging the valve past the stops. Continued pressure will, of course, seat the valve. The stops have been spaced therebetween so as to allow fluid to pass from the chamber out through the axial bore, if additional pressurizing fluid is desired.

A better understanding of this invention and the advantages which accrue therefrom will be had by a consideration of the detailed description herein, together with the acompanying drawings.

BRIEF DESCRIPTION OF THE DRAWINGS

In the drawings,

FIG. 1 illustrates a device for delivering a double-walled probe embodying the teachings of this invention and is shown in longitudinal, partially discontinuous, cross section;

FIG. 2 illustrates portions of the device of FIG. 1 after the probe has been partially everted into a body cavity;

FIG. 3 illustrates portions of the device of FIG. 1 wherein the probe is almost completely everted;

FIG. 4 illustrates portions of the device of FIG. 1 showing the seating of the annulus sealing valve, FIG. 5 illustrates the detachment of the pressurizing chamber of the device after the probe is fully emplaced and sealed;

FIG. 6 illustrates the attachment of a collection system to portions of the emplaced device;

FIG. 7 illustrates a second device for delivering a double-walled probe also embodying the teachings of this invention and shown in longitudinal, partially discontinuous cross section; and FIG. 8 illustrates the detachment of the pressurizing chamber and the sealing of the annulus using the device of FIG. 7 after the probe has been completely everted.

DETAILED DESCRIPTION OF THE INVENTION

Referring now to the drawings, FIG. 1 illustrates, in longitudinal cross section, a device 10 for everting a probe into a body cavity and embodying this invention, the device having generally an elongated cylindrical shape and FIGS. 2-6 illustrate the operation of this device. The device comprises a pressurizing chamber 12 provided with a port 14 for introducing fluid under pressure, the flow of which may be controlled by a valve 16. One end of the chamber 12 terminates in a nozzle 18 and has attached thereto an adapter 20 having an axial bore 22 therethrough in flow communication with the chamber 12 via the nozzle 18. The adapter is fitted to the nozzle so as to be in fluid tight connection but easily removable, this connection being accomplished by providing a semi-circular ridge 19 around the outer circumference of the nozzle which cooperates with a semi-circular groove 21 on the inside surface of the adapter. The flexible adapter can then be locked onto the nozzle by forcing the groove 21 over the ridge 19 and, similarly, may be disengaged by forcing the adapter away from the nozzle.

The forward tip 24 of the adapter is conically shaped and provided with yieldable tongues or petals 26 which are capable of parting so as to enlarge the opening 27 out of the adapter bore to permit the everting of the probe as will be further described herein. As shown in FIG. 1, the tip 24 of the adapter 20 is a separate piece which is permanently sealed to the remainder of the adapter at flanges 28 and 30 by means of heat sealing, adhesive sealing or the like. The two piece construction is preferred in that it is contemplated that the adapter will be constructed by the molding of an elastically resilient, flexible polymeric material and such a technique is best accomplished by molding separate pieces. It will be understood, however, that by using other fabricating methods, e.g., injection molding or casting, a one-piece adapter could be used.

Disposed within the device is a tube 36 which ultimately will form the everted probe. The tube 36, having an open end 35 and a closed end 46, is made up of contiguous portions comprising (sequentially from the open end 35) a relatively large diameter sheath 40, an enlarged central balloon 42 and a relatively small diameter conduit 44, the latter of which is closed at the terminal end 46. The open end 35 of the tube 36 is sealed at the circumferential portion 32 of the inner wall of the adapter tip, thereby closing the interior 37 of the tube to flow communication with the chamber and the bore of the adapter. This sealing also precludes fluid, introduced into the chamber through port 14, from flowing out of the tip opening 27 of the adapter in a manner unrestricted by the walls of the tube. Accordingly, by introducing pressurizing fluid into the chamber via valve 16 and port 14, fluid forces are induced to act upon a tube at the tip of the adapter, the forces being schematically depicted in FIG. 1 by the arrows labeled F. These forces then cause the tube to be everted past the yieldable tongues 26 of the tip of the adapter and out of the tip opening 27 in the form of a double-walled probe wherein the outside wall is the sheath 40 and the inner wall is the conduit 44.

The tube, partially everted into a body orifice 48, is illustrated in FIG. 2 and the fully everted tube is illustrated in FIG. 3. In connection with FIG. 3, it should be noted that the balloon portion 42, when the tubing is fully everted, acts as an enlargement of the annulus 49 between the sheath and the conduit and serves the function of a retention balloon as is used in the common retention catheter to lock the catheter into place within the bladder 45 of a patient.

Once the tubing is fully everted into a patient, it is desirable to break away the relatively large pressurizing chamber 12 leaving the fully inflated probe emplaced within the body orifice with only the relatively small adapter 20 depending therefrom. As described above, it is a simple operation to detach these two components, by simply pulling the chamber away from the adapter, i.e., the groove 21 in the flexible adapter is then forced over the ridge 19 of the nozzle 18 of the chamber thereby breaking the connection. The difficulty in accomplishing this disengagement step is that it is necessary to continuously maintain the annulus 49 of the probe in the pressurized state both during disengagement and thereafter. In particular, a seal must be provided to maintain pressuring fluid within the annulus 49 and the inflated balloon 42 of the probe. Referring again to FIG. 1 of the drawings, in accordance with this invention, a mechanically simple, yet highly effective sealing mechanism is provided. A valve 50 is provided near the closed end 46 of the conduit 44, the valve comprising a sphere having a cylindrical bore 52 therethrough. Preferably, the diameter is not greater than the outside diameter of the conduit and still more preferably is somewhat smaller than the conduit so that the conduit portion may be force-fitted through this bore and the valve 50 will remain in place and be carried on the conduit as it is drawn out through the device when the tube is everted. It is desirable that the valve be slidably adjustable with respect to the end 46 of the conduit during manufacturing. Preferably, the valve is then permanently affixed in its adjusted position by using, for example, a suitable adhesive. A valve seat 54 is provided in the inner wall of the adapter 20 at a position near the tip 24 and is adapted to cooperate with the valve 50 after the tube has been everted. The valve seat is sized so that its smallest cross sectional dimension is smaller than the largest cross sectional diameter of the valve when the adapter is in a relaxed state. Valve stops 56 are provided, projecting from the inner wall of the adapter at a point between the valve seat 54 and the chamber-end of the adapter. These stops comprise a plurality of spaced, thin, flexible, inwardly directed projections, circumferentially arranged around the inner wall of the adapter and are designed to temporarily inhibit the passage of the valve 50. They serve as a control point during the emplacement of the catheter and allow the flow of further amounts of pressurizing fluid if so desired, as will be described herein.

The operation of the annular sealing system is best described in connection with FIGS. 2–5. As shown in FIG. 2, the tube has been partially everted under the action of pressurizing fluid into the form of a double-walled probe, the annulus 49 of which is filled with pressurizing fluid. The retention balloon 42 is still wholly within the device, as is the conduit 44, although it has been drawn to an extent through the device, carrying with it the valve 50.

In FIG. 3, the eversion step is almost completed and the sheath 40 has been fully everted, the retention balloon 42 is now everted outside the sheath and almost completely inflated and the conduit 44 is almost entirely within the everted sheath with the exception of a small portion at the terminus thereof which still remains in the device.

Thus, in FIG. 3, the eversion process has proceeded to a point where the valve 50 has been carried up to and against the stops 56 which temporarily resist further eversion of the probe and forward movement of the valve. Sensing this resistance, the doctor inserting the tube will be apprised of the fact that the tube is essentially fully everted and that it is now time to terminate the pressurizing of the chamber 12 by, for example, closing valve 16. At this point in time, the doctor may also assure the completion of the eversion process and the filling of the retention balloon and annulus by allowing a small increment of additional pressurizing fluid to flow through valve 16. It will be understood that while the stops 56 temporarily restrain the valve 50, there are spaces therebetween through which this additional increment of pressurizing fluid may flow into the everted tube. Upon closing valve 16, the next procedure is to seal the annulus 49 in preparation for the removal of the chamber 12. Because, in accordance with the teachings of this invention, the adapter is constructed of a flexible, resiliently elastic material, the doctor can accomplish this annulus sealing by merely applying pressure with his fingers to the portion of the adapter immediately behind the valve 50, thus pushing the valve forward past the stops 56 and into the valve seat 54. This procedure is illustrated in FIG. 4, showing the point in time where the valve is finally seated, The resiliently elastic material of the adapter will then return to its original position leaving the valve tightly seated and the annulus sealed. While the valve seat 54 may be no more than a restriction in the adapter bore which makes essentially a single, continuously circumferential line contact with the valve 50, it is preferred, for the purpose of achieving a safely sealed annulus, to provide more than single line contact. This is accomplished, in the preferred embodiment of the invention by providing a constriction in the bore of the adapter (i.e., the diameter of the bore, at the forward end of the adapter, is smaller than the diameter of the valve 50) and providing a valve seat 54 comprising an arcuate groove, the radius of which is smaller than the radius of the valve 50, thus assuring two circumferential line contacts when the valve is seated.

Referring to FIG. 5, the doctor, having now seated the valve, may safely remove the cumbersome pressurizing chamber 12 (shown in phantom lines) by simply pulling it away from the adapter 20, as indicated by the horizontal arrow in FIG. 5, whereby the groove 21 in the adapter will ride over and unlock from the ridge 19 on the chamber nozzle 18.

It should be noted that, in the case of a urinary catheter, generally immediately upon the catheter entering the bladder, urine will begin to flow into the conduit, but will, of course, be restricted in that the conduit has a closed end 46. To open the conduit for urine flow, all that is required is for the doctor to snip off the tip of the now exposed end 46 of the conduit as is indicated in FIG. 5 by the vertical arrows. The preclude premature flow of urine, a clip 53 may be first inserted upstream of end 46 which can be released after end 46 is snipped off. This procedure of clipping and then opening the conduit is facilitated by having the conduit extend to an extent beyond the projecting end of the adapter so as to be readily accessible to the doctor. It is apparent then that by providing a valve 50 which can be slidably positioned on the conduit, the manufacturer may adjust the degree of the extension of the conduit from the adapter to whatever extent he finds convenient.

FIG. 6 illustrates the probe delivery device of this invention, as integrated with a collection system. Collection bag 55 is provided with the normally associated inlet tubing 57. The end of the inlet tubing is provided with a connector having a circumferential ridge 58 adapted to cooperate with the adapter of the probe delivery device of this invention. This ridge 58 is of a design similar to the ridge 19 on the nozzle 18 of the pressurizing chamber and in a like manner, cooperates with the groove 21 in the adapter and removed therefrom by merely pushing or pulling the parts together or apart.

In operation, after the probe is everted and the valve seated, the conduit extending from the adapter may be clipped closed, end 46 snipped off, the conduit inserted into the inlet tubing 56 of the collector bag 54, the clip removed and the adapter and inlet tubing locked together. All of these steps are advantageously accomplished without urine ever flowing anywhere but into the collector bag.

FIG. 7 illustrates, in longitudinal cross section, a second device 60 for everting a probe into a body cavity and represents a second embodiment of this invention. The device 60 comprises a pressurizing chamber 62 provided with a port 64 and a valve 66 for introducing and controlling the flow of pressurizing fluid into the chamber. The chamber 62 terminates at one end in a nozzle 68 and has attached thereto an adapter 70 having an axial bore 72 therethrough in flow communication with the chamber 62 via the nozzle 68. The adapter is fitted to the nozzle so as to be in fluid tight connection but easily removable. As shown in FIG. 7, this connection is merely a friction fitting, although the ridge and groove connection described with respect to the device of FIG. 1 may also be used.

The forward tip 74 of the adapter is conically shaped and provided with yieldable tongues or petals 76 which are capable of parting so as to enlarge the opening 77 and permit a tube to evert in the manner already described above. As shown in this embodiment, the tip 74 is molded integrally with the remainder of the adapter. However, a two-piece construction is also possible.

Disposed within the device 70 is a tube 78 which will ultimately form the everted probe. The tube 78, as in the prior embodiment, has an open end 80, a closed end 82 and contiguous portions (sequentially from the open end 80) comprising a sheath 84, a balloon 86, and a conduit 88. While the tube 78 may be molded or otherwise fabricated in one continuous piece, as shown in this instant embodiment, the sheath and balloon are molded separately from the conduit and then these parts are joined by heat sealing or adhesive means, for example. As in the prior embodiment, the open end 80 of the tube 78 is sealed across the bore of the adapter so that the pressurizing fluid will cause the tube to evert in the form of a double-walled probe.

The eversion process in this embodiment is similar to that described above with the concomittant problem of sealing the annulus of the everted double-walled tube prior to removing the pressurizing chamber 62. Accordingly as in the prior embodiment, a valve 90 is provided on the conduit near the closed end 82 and is adapted to cooperate with a valve seat 92 provided in the inner wall of the adapter bore. In this instant embodiment, however, the adapter, again being of a flexible, elastically resilient matter is fitted over the nozzle 68 of the chamber so as to be in a flexed condition. The valve seat 92, having a shape adapted to tightly receive the valve 90 when the adapter is in a relaxed state is, when the adapter is fitted over the nozzle of the chamber, in a flexed, enlarged state, i.e., larger than the valve 90. This flexing or stretching of the adapter so as to enlarge the valve seat is accomplished by the combination of choosing a material of construction for the adapter which is elastically resilient and providing the nozzle of the chamber of a diameter sufficient to stretch the adapter when the latter is fitted thereon. Preferably, it is desirable that the nozzle be provided with a portion 94 which extends into the adapter bore in close proximity to the valve seat and aids in maintaining the valve seat in the enlarged state.

The device, as illustrated in FIG. 7 is ready for everting the tube 78 into a body orifice. As in the prior embodiment, pressurizing fluid is introduced through valve 66 and port 64 into the device and the tube, in double-walled configuration, is everted through the tip 74 of the adapter 70. The valve 90 is carried with the conduit into the adapter bore 72 and enters the valve seat, but, because the latter is in an enlarged state, the valve does not yet act as a seal for the annulus of the everted double-walled tube. It is now desirable to remove the pressurizing chamber while maintaining the annulus in a sealed condition. In accordance with this instant embodiment of the invention, the sealing is accomplished simultaneously with the removal of the pressurizing chamber.

Referring to FIG. 8, illustrated therein is a tube, fully everted into a body orifice 96, having the inflated balloon 86, the outer sheath 84, the inner conduit 88, and an annulus 95, therebetween. The device is shown with the pressurizing chamber (in phantom lines) having been just separated from the adapter, as by pulling these elements apart. Simultaneous with the removal of the chamber from the adapter and more specifically, with the removal of the nozzle from the adapter bore, the stretched, flexed, elastically resilient adapter returns to its relaxed state and the valve seat tends to close upon the valve, thereby sealing the annulus (the closing of the seat upon the valve being shown diagramatically in FIG. 8 by the vertical arrows).

The above described embodiments are meant to be illustrative of the invention and many variations may be made therein, as will occur to one skilled in the art, while still remaining within the scope of the teachings herein disclosed. It will be understood, for example, that to a large extent, the features of the illustrative embodiments are interchangeable and thus, a unitary molded tube may be interchanged with a two-piece tube; means to temporarily restrain the valve, as were described in connection with the first embodiment, may be used in connection with the second embodiment; and the collector system described in the first embodiment may similarly be used in the second embodiment.

The pressurized chamber of the devices of this invention may be constructed from any engineering material suitable for the above described purposes, e.g., metals, plastics or glass. Preferably, the chamber is transparent, and is, in the instances where it is desirable to sterilize the probe assembly, resistant to such sterilizing conditions. Particularly suitable materials may be, for example, such clear nonelastic plastics such as polymers of styrene, carbonates, acrylates, or co- and terpolymers. Examples of these may be polystyrene-acrylonitrile copolymer, polystyrene, polycarbonate, polymethyl methacrylate, or acrylonitrilebutadiene styrene terpolymer.

The probe tube and the adapter should generally be fabricated from a material which lends itself to the formation of thin-walled nonbrittle, tubular constructions. Examples of suitable materials are the polyurethanes (both esters and ethers) e.g., the reaction products of methylene bis-(4, phenyl isocyanate) and poly(-tertra methylene glycol), or polyethylene adipate; the polyolefins and their copolymers e.g., polyethylene-vinyl acetate copolymer; the silicone rubbers e.g., poly(dimethyl siloxane); vinyl polymers e.g., plasticized polyvinyl chloride; and the natural and synthetic polyisoprenes e.g., 1,4 cis-polyisoprene.

What is claimed is:

1. A device for delivering a double-walled probe having a pressurized annulus into a body cavity by the method of eversion, said device comprising:

a pressurizing chamber having an inlet port for introducing a pressurizing fluid therein;

an adapter having an axial bore therethrough, said adapter having proximal and distal ends and a resilient intermediate portion of a sufficient length to permit flexing and said adapter being removably attached at its proximal end to said pressurizing chamber;

an eversible tube having a closed and an open end, said open end being sealed to the distal end of said adapter bore precluding the unrestricted flow of pressurizing fluid from said chamber out of said adapter, the remainder of said tube extending through said adapter bore and into said chamber;

valve means carried on said tube near said closed end thereof; and means in said adapter adjacent its distal end for seating said valve means to seal said pressurized annulus after said tube has been everted through said adapter, whereby when said resilient intermediate portion of said adapter is flexed said adapter bore is reduced in size thereby urging said valve means into said seating means.

2. The device of claim 1 wherein flexing means are provided for maintaining said adapter in the flexed state and said valve seat flexed to a size larger than said valve means whereby said valve may be carried into said enlarged seat upon everting said tube, said flexing means removed, with said valve seat relaxing about said valve means.

3. The device of claim 2 wherein said flexing means comprise said pressurizing chamber terminating in a nozzle, said adapter bore being fitted over said nozzle and in flow communication through said nozzle with said chamber, said nozzle being sized to maintain said adapter bore in a flexed condition and enlarge said valve seat when said adapter is fitted over said nozzle.

4. The device of claim 1 wherein said valve means is spherical and said valve seat comprises a circumferential groove in the inner wall of the bore of said adapter.

5. The device of claim 4 whereby the groove has a concave radius no greater than the radius of the valve.

6. The device of claim 1 wherein means are provided on the inner walls of said axial bore for temporarily restraining said valve means before it reaches said valve seat, said means comprising at least one thin flexible projection depending inwardly from the inner wall of said axial bore.

7. The device of claim 6 wherein said means comprise a plurality of projections arranged circumferentially about the inner wall of said axial bore and provided with spaces therebetween to allow pressurizing fluid to pass from said chamber out of said axial bore.

8. The device of claim 1 having said valve means carried on said tubing at a distance from the closed end of said tubing sufficient to allow said closed end to protrude from said adapter bore after said pressurizing chamber is removed whereby said closed end is available for opening.

* * * * *